(12) United States Patent
Braeckmans et al.

(10) Patent No.: US 8,928,875 B2
(45) Date of Patent: Jan. 6, 2015

(54) METHODS AND SYSTEMS FOR OPTICAL CHARACTERISATION

(75) Inventors: Kevin Braeckmans, Daknam (BE); Hendrik Deschout, Ghent (BE); Kristiaan Neyts, Ghent (BE); Joseph Demeester, Ghent (BE); Stefaan De Smedt, Mariakerke (BE)

(73) Assignee: Universiteit Gent, Ghent (BE)

( * ) Notice: Subject to any disclaimer, the term of this patent is extended or adjusted under 35 U.S.C. 154(b) by 151 days.

(21) Appl. No.: 13/516,050

(22) PCT Filed: Dec. 17, 2010

(86) PCT No.: PCT/EP2010/070119
§ 371 (c)(1),
(2), (4) Date: Aug. 7, 2012

(87) PCT Pub. No.: WO2011/073410
PCT Pub. Date: Jun. 23, 2011

(65) Prior Publication Data
US 2012/0293797 A1    Nov. 22, 2012

(30) Foreign Application Priority Data

Dec. 17, 2009    (GB) .................................. 0921994.0

(51) Int. Cl.
*G01N 21/03*    (2006.01)
*G01N 21/05*    (2006.01)
*G01N 21/64*    (2006.01)
*B01L 3/00*    (2006.01)

(52) U.S. Cl.
CPC ............ *G01N 21/05* (2013.01); *G01N 21/6458* (2013.01); *B01L 3/502715* (2013.01); *G01N 21/0303* (2013.01); *G01N 2021/0346* (2013.01)
USPC ............................ 356/246; 356/445; 385/129

(58) Field of Classification Search
CPC .............. G01N 21/05; G01N 21/6458; G01N 21/0303; G01N 2021/0346; B01L 3/502715
USPC .......... 356/246, 432–437, 445; 436/535, 164, 436/170–172; 422/82.05–82.11; 385/12, 385/14, 30, 37
See application file for complete search history.

(56) References Cited

U.S. PATENT DOCUMENTS 5,677,196 A * 10/1997 Herron et al. ................. 436/518
6,239,876 B1 * 5/2001 Brandenberg ................ 356/481
6,438,279 B1  8/2002 Craighead et al.
(Continued)

FOREIGN PATENT DOCUMENTS

WO      2004/040319 A1    5/2004

OTHER PUBLICATIONS

International Search Report for PCT/EP2010/070119, Mar. 15, 2011.
(Continued)

*Primary Examiner* — Sang Nguyen
(74) *Attorney, Agent, or Firm* — Bacon & Thomas, PLLC

(57) ABSTRACT

An optical device is described for irradiating at least one object in a medium. The optical device may be a microfluidics device, and comprises at least one integrated planar waveguide that enables providing sheet irradiation of objects in the medium. A characterization system including such an optical device and a corresponding method of characterizing an object or a fluid are described.

17 Claims, 15 Drawing Sheets

(56) References Cited

U.S. PATENT DOCUMENTS

| | | | |
|---|---|---|---|
| 6,970,249 B1* | 11/2005 | Lipson et al. | 356/445 |
| 7,619,739 B1* | 11/2009 | Sutherland et al. | 356/432 |
| 7,920,267 B2* | 4/2011 | Cho et al. | 356/445 |
| 8,279,445 B2* | 10/2012 | Dominguez Horna et al. | 356/477 |
| 8,325,347 B2* | 12/2012 | Cottier | 356/477 |
| 2004/0081384 A1* | 4/2004 | Datesman et al. | 385/12 |
| 2006/0251371 A1* | 11/2006 | Schmidt et al. | 385/129 |
| 2007/0115455 A1 | 5/2007 | Ilev et al. | |
| 2007/0146701 A1* | 6/2007 | Kiesel et al. | 356/317 |
| 2010/0065726 A1* | 3/2010 | Zhong et al. | 250/227.24 |

OTHER PUBLICATIONS

Yin, D., "Microphotonic control of single molecule fluorescence correlation spectroscopy using planar optofluidics", Optics Express, vol. 15, No. 12, Jun. 11, 2007, XP002626169.

* cited by examiner

METHODS AND SYSTEMS FOR OPTICAL CHARACTERISATION

FIELD OF THE INVENTION

The invention relates to the field of optical detection and/or characterization of materials. More particularly, the present invention relates to methods and systems for providing irradiation of materials, such as for example to detect properties of particles in a gaseous or liquid medium or properties of the corresponding medium transporting them.

BACKGROUND OF THE INVENTION

Characterisation of materials and objects based on an optical response by the objects when irradiated by a suitable irradiation source is widely spread in the biophysical, biochemical and biopharmaceutical fields. Some examples thereof are dynamic light scattering, single molecule spectroscopy or single particle tracking microscopy. In fluorescence single particle tracking (fSPT), for example, fluorescence light emitted by fluorescent particles upon irradiation by an excitation source is detected by a fluorescence microscope and a digital camera. By imaging the movement of the particles when dispersed in a solution, it is possible to calculate the diffusion coefficient and hence the size of the individual particles. Such experiments are typically based on normal epi-fluorescence illumination, providing a low signal to background ratio due to out of focus fluorescence which can reach the detector because of a limited confinement of the excitation beam and the detection volume. Basically two strategies have been proposed to avoid light from reaching the detector that is coming from other parts of the sample than the actual focal plane. The first strategy is based on increasing the confinement of the detection volume. This is being used in the classic field of confocal microscopy. The second strategy is based on increasing the confinement of the excitation volume. This is the basic motivation for multi-photon microscopy where excitation of fluorophores will only occur in the focal spot of the focused laser beam, which has a volume of less than a femto-liter. Imaging of the sample is then achieved by scanning the laser focus across the sample in a raster pattern, hence limiting the maximal image acquisition rate. Another solution is provided by Ritter et al. Ritter et al. describe in Optics Express 16 (2008) page 7142 a high resolution selective plane illumination microscope whereby confinement along the optical axis of the detection path is achieved by illuminating the sample from the side with a thin plane or sheet of light. The selective plane excitation, which could also be referred to as sheet illumination, allows reduction of the background noise due to the fact that no excitation is performed in parts of the object not of interest. Reduction of background noise results in a significantly higher contrast, which results in an improved detection sensitivity. The selective plane excitation as described is created by creating a sheet like illumination using a set of optical elements including a cylindrical beam expander combined with an objective lens for generating a sheet like illumination.

SUMMARY OF THE INVENTION

It is an object of embodiments of the present invention to provide good methods and systems for optical detection and/or characterisation. It is an advantage of embodiments according to the present invention that optical detection and/or characterisation techniques can be obtained having a good depth resolution by confinement of the irradiation volume. It is an advantage of embodiments of the present invention that good research tools can be made for measuring particle properties, e.g. particle properties in suspensions. It is an advantage of particular embodiments of the present invention that these allow measurements of particles at the single particle level, such as e.g. their size and/or zeta potential. It is an advantage of particular embodiments of the present invention that these can replace or complement dynamic light scattering and relax the required conditions of ensemble measurements of high concentrations of particles in pure solutions, thus providing a technique that is more widely applicable.

It is an advantage of embodiments according to the present invention that by integration of the planar waveguide in the opto-fluidics device, no alignment issues can arise with respect to alignment of the waveguide as function of the sample. It is an advantage of embodiments according to the present invention that a thin illumination sheet can be provided, such that a better contrast and lower detection limit can be obtained as compared to 'normal' irradiation, i.e. irradiation substantially parallel to the optical axis of the detection system.

It is an advantage of embodiments according to the present invention that small sample volumes are sufficient for characterization as the measurement volume can be in the order of 1 nano liter. It furthermore is an advantage that, by transporting different parts of the sample to the observation area, a plurality of samples can be imaged in an automatic and/or automated manner, allowing to perform efficient measurements and to obtain a high amount of data for statistically relevant results.

It is an advantage of embodiments according to the present invention that the system can be obtained as a lab-on-a-chip system, and therefore may be combinable with other lab-on-a-chip technologies, such as for example blood-cell separation technology.

Embodiments of the present invention may for example be provided as add-on modules to existing optical systems, such as for example fluorescence microscopes, but also may be part of an integrated optical system including light sources, optics, detectors and optionally also software.

The above objective is accomplished by a method and device according to the present invention.

The present invention relates to an optical device for irradiating at least one object in a medium, the optical device comprising at least one integrated planar waveguide, wherein the integrated planar waveguide is arranged for providing sheet irradiation into a measurement region. It is an advantage of embodiments according to the present invention that sheet irradiation can be provided with a very thin irradiation sheet, resulting in good contrast and a good detection limit. The at least one integrated waveguide may have a height in a first direction perpendicular to the propagation direction of radiation in the at least one integrated waveguide, the height being at least three times smaller than a width in a second direction perpendicular to the propagation direction of radiation in the at least one waveguide. The device may be configured for detection of a response signal from the at least one object being irradiated in the measurement region. It is an advantage of embodiments according to the present invention that an illumination sheet is obtained with substantially homogeneous characteristics, e.g. a substantially constant thickness, in the measurement region, i.e. at least in a direction of the width of the integrated waveguide. It is an advantage of some embodiments according to the present invention that the sheet illumination can stem from a single radiation output from the integrated waveguide. The sheet illumination may have a height to width ratio of at least 1 to 3, more advantageously at least 1 to 5, more advantageously 1 to 10 or 1 to 20.

The integrated waveguide may be adapted for supporting a single mode of a laser. The latter may advantageously result in confinement of the sheet with respect to its thickness over a larger surface area.

The optical device may be configured for allowing detection of a response to the sheet irradiation in a direction perpendicular to the irradiation sheet.

The sheet irradiation may be used for imaging one or more objects in the medium.

The device furthermore may comprise at least one sample chamber in which the medium comprising the at least one object of interest can be dispensed, the measurement region being in contact with the planar waveguide such that a sheet of irradiation is generated within the channel or part thereof forming the measurement region. The sample chamber may correspond with at least part of the transportation channel.

The device furthermore may comprise at least one transportation channel for transportation of the medium comprising the at least one object of interest, when the medium is a fluidic sample, the transportation channel containing or being in contact with the planar waveguide such that a sheet of irradiation is generated within the channel or a part thereof forming the measurement region. It is an advantage of embodiments according to the present invention that the sample can be in direct contact with the planar waveguide, allowing efficient illumination of the sample.

The optical device may be an opto-fluidics device, the transportation channel may be an integrated microfluidics channel, and the measurement region may be part of the integrated microfluidics channel of the opto-fluidics device. The integrated planar waveguide may have an outcoupling region in the transportation channel.

The device may comprise an integrated irradiation source.

The optical device furthermore may comprise electrodes for providing an electric field in a direction substantially perpendicular to a transportation direction of the at least one object of interest.

The optical device may comprise at least one manipulation site for manipulating the object of interest and the optical device being arranged for inducing sheet irradiation at different positions in the measurement region so as to characterise effects of the manipulation.

The optical device may comprise a plurality of measurement regions, whereby the device may be adapted for imaging a plurality of objects in different measurement regions.

The optical device may comprise two integrated waveguides at opposite sides of the measurement region, configured so that their sheet illumination may or may not at least partly coincide. Alternatively, the integrated waveguide at the opposite side may be used to collect light that is transmitted from the irradiating waveguide and/or light that is scattered or actively generated from the at least one illuminated object. The at least one integrated planar waveguide may have a core defined by two major surfaces, wherein none of the major surfaces lies in plane with the bottom or top surface of the transportation channel. It is an advantage of embodiments according to the present invention that the irradiation sheet generated in the waveguide does not irradiate a bottom or top of the transportation channel.

The optical device may comprise a substrate layer, with on top an integrated planar waveguide and a second component attached to the substrate layer of the integrated waveguide, e.g. using glue, and the integrated planar waveguide and second component being spatially configured so that the transportation channel is substantially formed from the substrate layer, the integrated planar waveguide and the second component.

The present invention also relates to a characterisation system for characterising at least one object in a medium, the characterisation system being adapted for co-operating with or comprising an optical device as described above, the characterisation system comprising a radiation source for generating a radiation beam for irradiating the at least one object using said optical device and a detection system for detecting a response due to interaction of the at least one object with the irradiation sheet generated using the optical device.

The detection system may be configured to detect the signal in a direction substantially perpendicular to an average plane through the irradiation sheet.

The detection system may be configured so that the focal plane of the detection system for capturing the detection signal coincides with the irradiation sheet.

The system furthermore may comprise a coupling means for coupling radiation into the waveguide of the optical device.

The radiation source may be integrated in the optical device.

The present invention also relates to the use of an optical device as described above or a characterisation system as described above, for deriving physicochemical properties of objects in a fluid or of a fluid transporting the objects.

The present invention also relates to the use of an optical device as described above or a characterisation system as described above for imaging a slice of an object, i.e. optical sectioning The present invention furthermore relates to a method for characterising an object in a medium, the method comprising generating sheet irradiation in a measurement region using an integrated planar waveguide, providing interaction between the sheet irradiation and the at least one object to be characterised, and detecting a signal in response to the interaction between the sheet irradiation and the object of interest. The method furthermore may comprise coupling a radiation beam in the integrated planar waveguide.

The present invention also relates to a method for manufacturing an optofluidic device, the method comprising providing a substrate layer, providing on the substrate layer an integrated planar waveguide, and positioning a second component by fixing it in a separate step with respect to the integrated planar waveguide, such that the integrated planar waveguide, the second component and the substrate form a transportation channel whereby at least part of the transportation channel can be illuminated using the integrated planar waveguide.

Particular and preferred aspects of the invention are set out in the accompanying independent and dependent claims. Features from the dependent claims may be combined with features of the independent claims and with features of other dependent claims as appropriate and not merely as explicitly set out in the claims. These and other aspects of the invention will be apparent from and elucidated with reference to the embodiment(s) described hereinafter.

Figure 1:
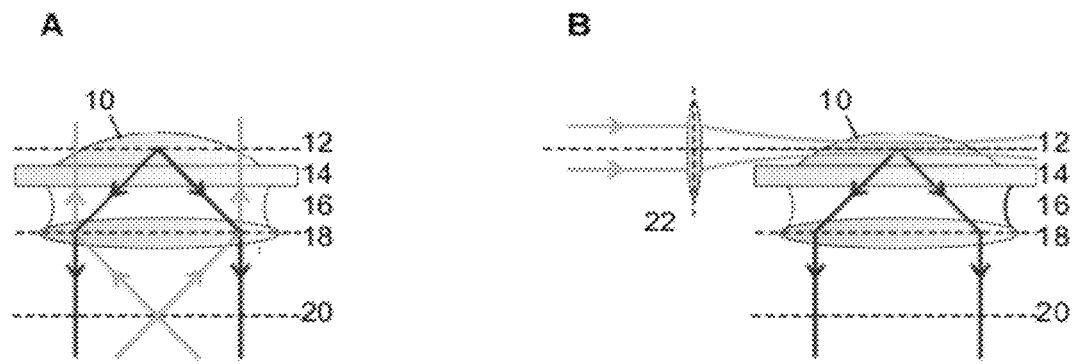
FIG. 1 illustrates the difference between epi-illumination (A) and sheet illumination (B) that can be used in embodiments according to the present invention.

The drawings are only schematic and are non-limiting. In the drawings, the size of some of the elements may be exaggerated and not drawn on scale for illustrative purposes.

DETAILED DESCRIPTION OF ILLUSTRATIVE EMBODIMENTS

Where in embodiments according to the present invention reference is made to "optical" or "opto" or "illumination" or "irradiation", such terms are intended not only to encompass optical radiation but to encompass all types of electromagnetic radiation that could be used for characterization, such as for example, infrared (IR) radiation, visual (VIS) radiation, ultraviolet (UV) radiation, etc.

Where in embodiments of the present invention reference is made to "sheet irradiation", reference is made to irradiation whereby the generated irradiation field has a region in one direction in which it is substantially less extended compared to the other directions, such that the irradiation occurs in a sheet-like shape. Advantageously sheet irradiation is obtained in at least the region corresponding with the field of view of the detection system used. The height of such a region in the irradiation sheet may be at least 3 times, more preferably at least 4 times smaller than the length and width of the irradiation field formed. In advantageous embodiments the height, also referred to as the thickness, of the sheet in the region may be between 1 to 50 µm, advantageously 1 to 10 µm, or more advantageously 1 to 5 µm. The width and length of the irradiation sheet may for example be between 10 µm and 500 µm.

Where in the present invention reference is made to a planar waveguide, typically reference may be made to a waveguide with a planar geometry, guiding the light substantially in a direction along the average plane following the planar geometry. The height of the waveguide is advantageously may be at least three times smaller than a width, advantageously at least 4 times smaller than a width in a second direction perpendicular to the propagation direction of radiation in the waveguide. Where in embodiments of the present invention reference is made to "integration" or "integrated", reference is made to monolithically, heterogeneously and/or hybridly integration. Monolithical integration is the integration technology that uses a single processing flow to process the diverse components potentially using different materials. Heterogeneous integration is the integration technology for which the components are processed in separate process flows, which are then integrated at die or wafer level, e.g. BCB bonding, wafer bonding, and other bonding schemes, such as 3D integration. Hybrid integration is the integration of components or materials on processed substrates, e.g. flip-chipping of detectors, bumping, glueing, wire bonding, co-packaging, etc.

In one aspect, the present invention relates to an optical device for irradiating at least one object in a medium. The object may be any type of object for which characterisation may be performed. Embodiments of the present invention especially are advantageous for obtaining individual particle or object properties.

Where in embodiments of the present invention reference is made to an optofluidics device, reference is made to an optical device comprising an integrated fluidics or microfluidics channel. Typically a fluidic medium may be transported or kept in such a channel. In embodiments of the present invention such a channel may be referred to as the transportation channel.

The medium may be a fluid, gas or solid material in a measurement region which may be positioned in or outside the device and may be a sample room, compartment or an open measurement region close to or adjacent the optical device. The medium may be transported or positioned in a transportation channel and the measurement region may be positioned in the transportation channel. The transportation channel may at least partly take the form of a sample chamber, measurement chamber, a channel, . . . . The transportation channel can extend from one side of the optical device to another side thereof or may be positioned only in a limited portion of the optical device, thus rather forming a closed chamber. The transportation channel may be an integral portion of the optical device. Some embodiments are especially suitable for characterising for example single particle properties of a set of particles suspended in a fluid. The device may be especially suitable for use with imaging or characterization systems or methods described in the other aspects. In some applications the device may be used for determining properties of small objects, such as micro or nano-sized objects, e.g. particles with an average size or diameter between 1 nm to 10 µm. The optical device according to embodiments of the present invention comprises an integrated waveguide to produce sheet irradiation for irradiating the at least one object in the medium. An advantage of devices according to embodiments of the present invention is the generation of selective planar irradiation of objects. The device may be adapted for detection of the objects or parts thereof performed in a direction perpendicular to the irradiation plane (z-direction). The difference between epi-illumination (A) and sheet illumination (B) is by way of illustration shown in FIG. 1. In FIG. 1 (A), an epi-illumination and detection setup is shown for detecting features in a sample 10, wherein the focal plane 12, a cover glass 14 for carrying the sample 10, an immersion medium 16, an objective lens 18 and a back focal plane 20 are indicated. In FIG. 1 (B) the same components of the detection are indicated, but combined with a sheet type illumination, in the present drawing illustrated by use of a cylindrical lens 22. It can be seen that the excitation or scattering according to embodiments of the present invention is limited to a confined region of the sample, whereas in epi-illumination this is not the case.

In other words, sheet irradiation has the advantage that only one, some or a portion of the object(s) in the medium are irradiated, resulting in the possibility of detection with a reduced background signal, improved contrast and a lower detection limit, when using detection in response to the irradiation sheet in a direction substantially perpendicular to the irradiation plane. The latter may for example be caused by the lack of optical response of objects or medium in the neighbourhood of the irradiated plane because of the absence of irradiation in these areas. The response generated by the objects in response to being irradiated, can be elastic or inelastic scattered light or a secondary signal that is produced by the object after (partial) absorption of the irradiation, such as fluorescence, stimulated emission, luminescence, phosphorescence, coherent anti-stokes Raman scattering etc.

In one embodiment, the optical device is combined with, for example, a micro-CCD head or fibre-optic imaging bundle, and the device is used as a miniature probe for obtaining confocal-like images in applications such as non-destructive testing, remote visual inspection or process analytical technology. Such a device allows obtaining confocal-like images of objects suspended in gas or liquid at CCD camera imaging rates. This is advantageous, especially in contrast to the inherently slower classic confocal approach in which a point of light has to be scanned across the sample to sequentially build up an image.

In one embodiment, the optical device is an opto-fluidics device having a transportation channel whereby the at least one integrated planar waveguide is adapted for providing sheet illumination into the fluid channel. The microfluidics device may be especially suitable for imaging or characterization of particles in the fluid or objects suspended in the fluid. The at least one fluid channel may be a plurality of fluid channels, whereby the plurality of fluid channels may be separate channels or may be linked to each other such that an evolution of the objects in the fluid can be followed, when the fluid runs through the subsequent channels. A more particular example with respect thereto will be provided later by way of illustration. The microfluidics device may be a disposable microfluidics device, although embodiments of the invention are not limited thereto. It may be positioned in a microfluidics device holder, which may be referred to as cartridge, although embodiments of the invention are not limited thereto. As indicated above, an advantage of embodiments according to the present invention is that they allow obtaining high quality images of objects that are suspended in a fluid flowing through the microchannels.

Figure 2A:
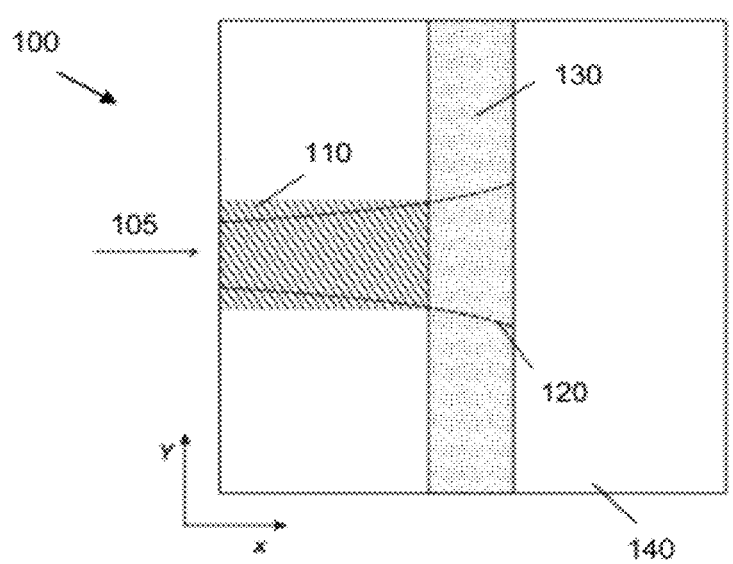
FIG. 2A and FIG. 2B illustrate a top view and side view of an optofluidics device according to an embodiment of the present invention.
Figure 2B:
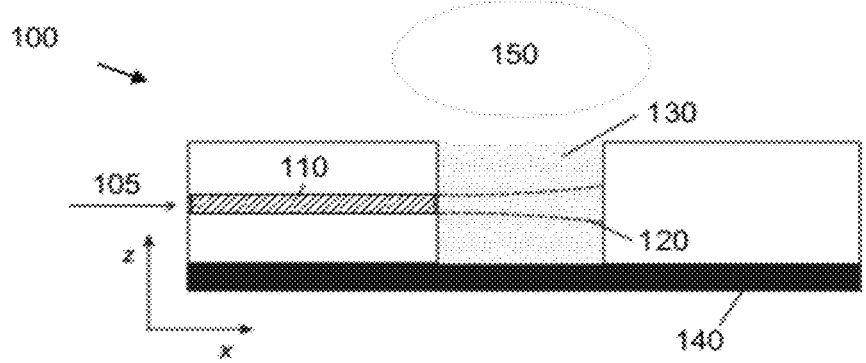

By way of illustration, the embodiments of the present invention not being limited thereto, further standard or optional features and advantages will be provided with reference to an exemplary microfluidics device, an example thereof shown in FIG. 2A en FIG. 2B.

The optical device 100 comprises at least one planar waveguide 110 to generate an irradiation sheet 120, also referred to as illumination sheet or light sheet, in a measurement region 130 in or near the device 100. The irradiation sheet 120 is caused by providing an irradiation beam 105 in a planar waveguide 110. The core of the planar waveguide 110 extending in a wave travelling direction, e.g. the x-direction, has a higher refractive index than the surrounding media and therefore confines the radiation in a height direction of the waveguide, e.g. the z-direction, and is wide in a width direction, e.g. the y-direction perpendicular to the z-direction. The height advantageously is the size of the component in the direction in which detection is performed. The width advantageously is the size of the component in the direction perpendicular to the height direction and perpendicular to the wave travelling direction. The waveguide may be a polymer waveguide, a dielectric waveguide, it can be based on low refractive index materials, wherein the difference in refractive index, e.g. between a cladding material and a core material, is limited to less than 1, e.g. to a few tenths or a few hundredths of a refractive index unit. In some examples, the waveguide may be based on a silicon on insulator material system, a III-V material system, metallic layers, dielectrics, glass or silica-based systems, or a combination thereof. The core of the fibre typically may have a higher refractive index that the cladding in order to confine the light in the neighbourhood of the core of the waveguide. The waveguide should preferably contain only a single mode in the vertical direction for the envisaged wavelength of radiation. Where the radiation exits the waveguide, the mode advantageously has a preferred thickness (z-direction) in the range of 1 to 10 µm.

In at least some embodiments according to the present invention, the core of the planar waveguide is defined by two major surfaces (extending substantially parallel with the substrate carrying the waveguide) and the waveguide is configured such that none of these major surfaces lies in plane with a bottom or top of the transportation channel. In other words, in some embodiments, the planar waveguide is positioned on the substrate that will form the bottom of the transportation channel and the waveguide comprises at least a cladding layer between the substrate and the core of the waveguide.

Where the radiation exits the waveguide in the measurement region, e.g. the fluid channel, a sheet of radiation is formed which is propagating in the x direction, narrow in the z-direction and more extended in the y direction. The irradiation sheet has a preferred thickness (z-direction) in the range of 1 to 10 µm and covers an area of at least 10 µm by 10 µm (xy observation region). Although an irradiation sheet which is thinner (z-direction) than one µm is also envisaged by embodiments of the present invention, such an irradiation sheet typically will become broad after a shorter distance due to stronger diffraction. An irradiation sheet which is thicker than 10 µm will diffract only slightly, but will lead to a larger area of irradiation.

Figure 3A:
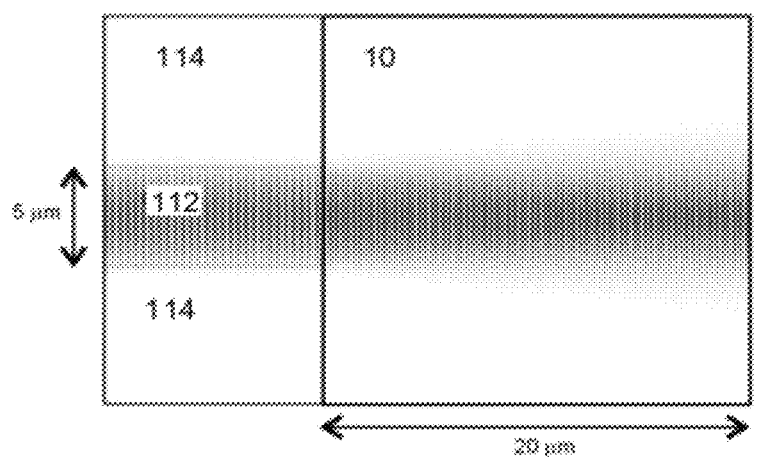
FIG. 3A and FIG. 3B illustrate a numerical simulation of a sheet of light and an intensity profile using a optofluidics device, according to an embodiment of the present invention.
Figure 3B:
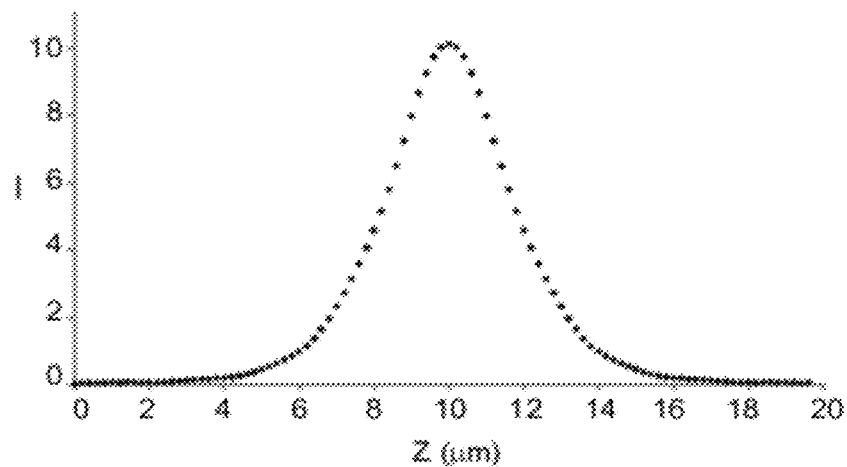

FIG. 2A and FIG. 2B show standard and optional features of embodiments according to the present invention, wherein an irradiation beam 105, e.g. a laser radiation, is guided into a planar waveguide 110 and thus provided as sheet irradiation 120 into a measurement channel 130. The system typically is provided on a substrate 140. The detection system 150 advantageously may be positioned above the fluid channel 130. By way of illustration, an example of a numerical simulation is shown in FIG. 3A indicating that sheet illumination 120 can be created with a nearly constant thickness of approximately 5 µm (FWHM) over a distance of at least 20 µm in a measurement region using a planar waveguide with a low refractive index contrast. In the present example, the measurement region comprises water as sample 10. The planar waveguide 110 is also shown, with its core 112 and cladding regions 114. In FIG. 3B, the intensity profile shows the axial intensity distribution in the measurement region at 19.5 µm from the waveguide exit.

Figure 4A:
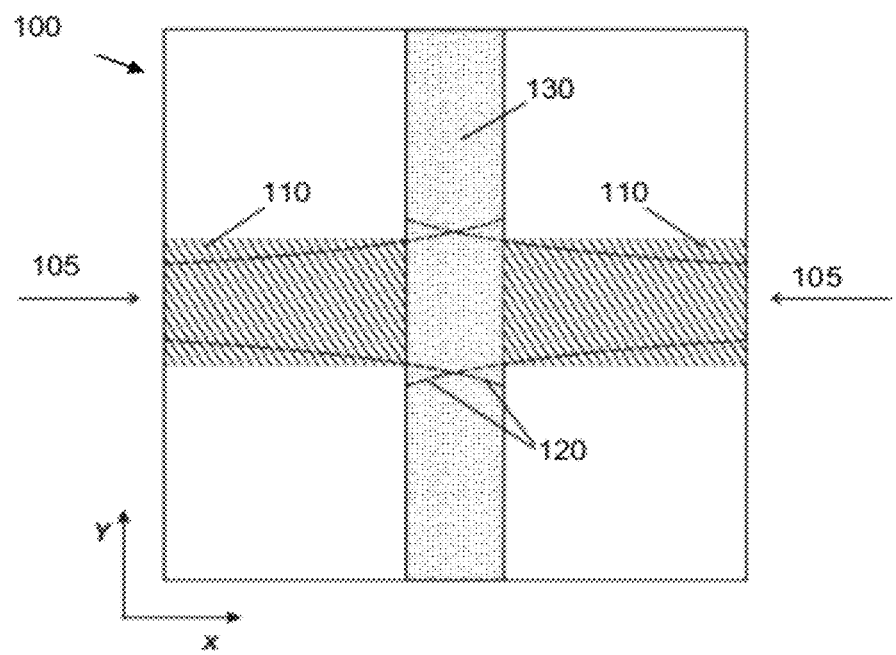
FIG. 4A and FIG. 4B illustrate an optofluidics device comprising two opposing waveguides and substantially coinciding illumination sheets, according to an embodiment of the present invention.
Figure 4B:
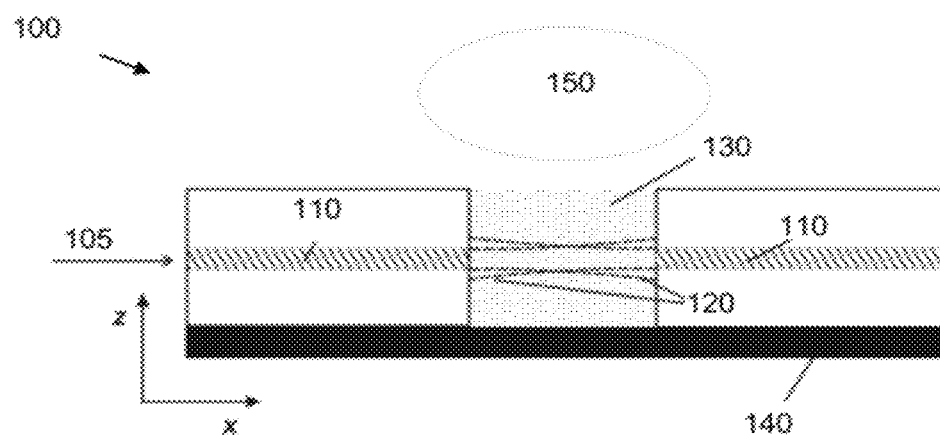
Figure 4C:
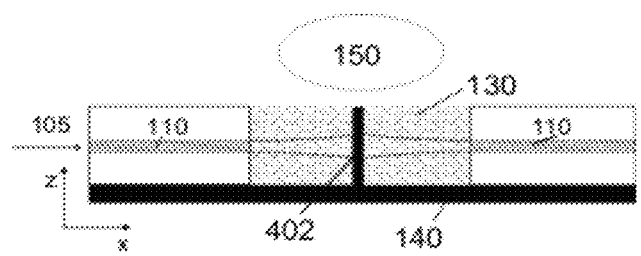
FIG. 4C illustrates an optofluidics device wherein two opposing waveguides are used, each for creating half of the illumination sheet in the fluidics channel, according to an embodiment of the present invention.
Figure 5A:
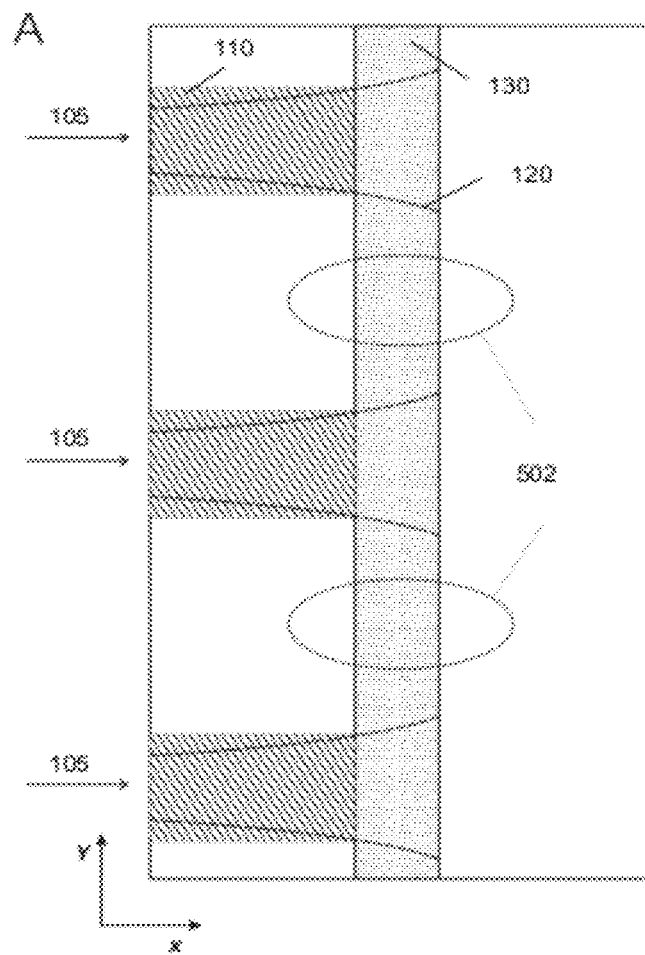
FIG. 5A and FIG. 5B illustrate optofluidics devices comprising multiple sheet illumination sites, either for probing different portions of the same fluid channel (FIG. 5A) or for probing different fluid channels (FIG. 5B).

The at least one planar waveguide also may be a plurality of waveguides imaging the same or different parts of the measurement region 130. In one example, the plurality of waveguides comprises two planar waveguides 110 provided opposite to each other such that, if radiation is fed to both waveguides, two opposing irradiation sheets 120 are formed coinciding in the measurement region 130 in the same plane. A corresponding device is shown in top view and side view in FIG. 4A and FIG. 4B. The latter may be advantageous to provide a more homogeneous irradiation distribution over the entire width of the measurement region 130, e.g. a channel. Furthermore, as some divergence may occur of the radiation beam forming the sheet irradiation, in one example the irradiation sheets may only be used for irradiating half of the measurement region. A structure 402 acting as an opaque screen in a central position of the measurement region of the device could be used, as indicated in FIG. 4C. In yet other examples of the optical devices or chips, a plurality of waveguides 110 or one or more splitted waveguides may be used for generating multiple irradiation sheets 120. In one example such multiple irradiation sheets 120 can be provided at different positions of the measurement region 130 to obtain multiple observation sites. The induced changes can be studied if, for example, intermediate on chip chemical or physical interactions can be induced, e.g. at interaction sites 502 positioned in between irradiation sheets 120 in the measurement region 130, e.g. a fluid channel. An example of such an optical device is shown in FIG. 5A. Alternatively, several planar waveguides for providing each an irradiation sheet 120 for a different measurement region 130, e.g. a different fluid channel, can also be obtained, as described in FIG. 5B. In this way, several samples can be characterized sequentially or in parallel using the same device.

Figure 6:
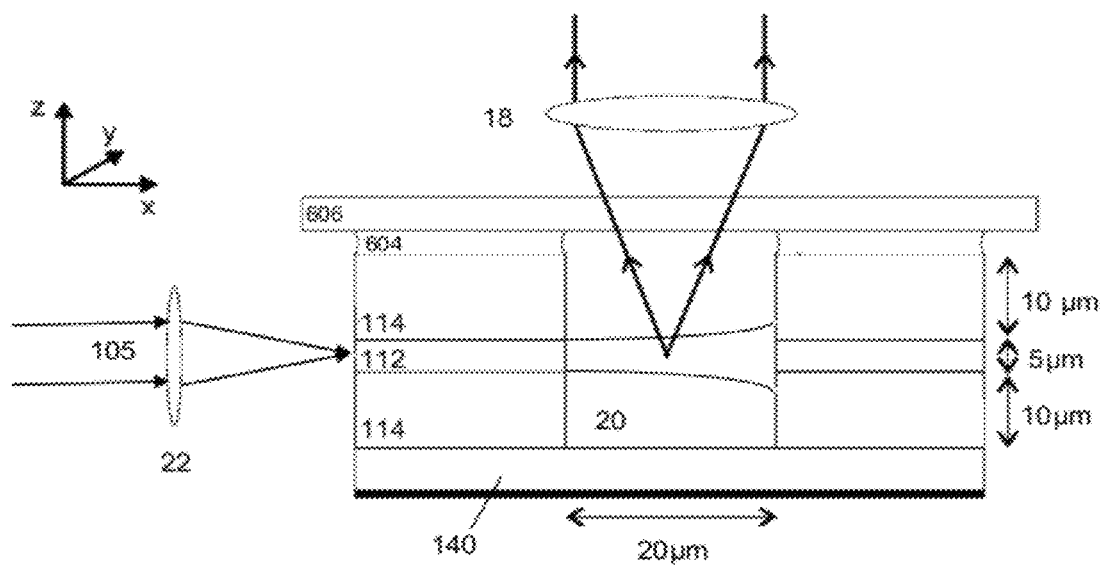
FIG. 6 illustrates a side view of an exemplary optofluidics device showing a particular planar waveguide, according to an embodiment of the present invention.

FIG. 6 illustrates a particular example of a device, whereby an optical device is shown having a planar waveguide 110 made of three layers of polymer material. The three layers, deposited on a substrate 140 are a stack of a cladding layer 114, a core 112 and a further cladding layer 114. In the present example the cladding layers 114 are approximately 10 µm thick while the core 112 thickness is approximately 5 µm. In the present example, embodiments of the present invention not being limited thereto, the optical device furthermore comprises a cover 602 being a microscope cover glass fixed to the cladding layer 114, e.g. glued using glue 604 to the cladding layer 114. The irradiation may be guided towards the optical device using a coupling lens 22, e.g. a cylindrical coupling lens, and the detection is performed by capturing a detection signal from the optical device using an objective lens 18 and a detector (not shown). According to some examples, the optical device can be an opto-fluidic chip, whereby a microfluidics channel in which an irradiation sheet is provided can be part of a more elaborate microfluidics chip that is designed for other tasks as well, such as biochemical assays, immunoassays and single cell analysis.

Turning back to FIG. 2A and FIG. 2B, the device furthermore comprises or is arranged to use a measurement region in or close, e.g. adjacent, to the integrated waveguide. The measurement region can be a channel, such as for example a fluid channel if a microfluidics device is used, a measurement room, a measurement compartment, a partially-open space close to or adjacent to the planar waveguide, etc. The measurement region is the region wherein the sample to be studied is provided or guided and where interaction with the irradiation sheet will take place. In some embodiments, the measurement region is one or more fluidic channels. The diameter and depth of such a fluidic channel 130 may be for example in the range of 1 to 1000 micrometer, although embodiments of the present invention are not limited thereto. Such a fluidic channel 130 may be provided in different shapes. In the measurement region, different chemical or physical interaction regions may be provided for allowing objects of interest to undergo chemical or physical interaction. The measurement region 130 may be made using any suitable technique such as for example by etching, moulding, depositing material on both sides of the channel, etc. By way of illustration, embodiments of the present invention not being limited thereto, an example of a manufacturing technique for an optofluidic device according to embodiments of the present invention wherein the channel is formed by positioning different substrates spaced from each other, thus forming the channel in between the substrates. Such a manufacturing technique has the advantage that accurate definition of the channel can be obtained and that different parts can be processed separately without affecting the other parts. Fluid may be transported in the measurement region, based on capillary forces, gravity or it may be pumped, using a pumping means. Such a pumping means may generate an overpressure at the entrance and/or an under-pressure at the exit to transport the fluid through the measurement region. The pumping means may also be part of the detection system rather than part of the optical device. As will be illustrated later, an electric field generator may be provided near the measurement region for performing control of the objects of interest, e.g. for performing electrophoresis measurements.

The waveguide 110 and measurement region 130 typically may be positioned on or form part of a substrate 140. Such a substrate 140 may be any suitable substrate that is compatible with the integrated planar waveguide 110. In some embodiments, the integrated planar waveguide 110 may be manufactured by depositing the planar waveguide 110 on the substrate 140, putting less stringent requirements on the selection of the substrate. In other embodiments, the integrated planar waveguide may be formed by processing part of the substrate 140, such that a larger compatibility between the integrated planar waveguide and the substrate are needed. The substrate may be a polymer substrate, a semiconductor substrate such as a silicon wafer, a metal substrate, a transparent substrate such as a glass or quartz substrate etc. The substrate also may comprise other layers, being of less relevance for the components positioned on the substrate or in part thereof.

The device 100 advantageously also may comprise a measurement region inlet and a measurement region outlet for receiving and removing the medium.

Other optional components which may be part of the optical device may correspond with components as present in optical devices and/or microfluidics devices, as known to the person skilled in the art.

In a second aspect, the present invention relates to a system for characterising objects in a fluid,—e.g. for imaging or deriving properties thereof—such as for example for characterising a plurality of objects for which there is interest in individual particle properties, or a larger object suspended in a fluid. The system is adapted for cooperation with or comprises an optical device as described in any of the embodiments of the first aspect. The system furthermore comprises a radiation source either external or integrated on the chip, optionally a coupling means for coupling radiation from the source into an integrated planar waveguide for generating sheet irradiation, and a detector for detecting in a direction substantially perpendicular to the average plane through the sheet irradiation a detection signal responsive to the generated sheet irradiation.

Figure 7:
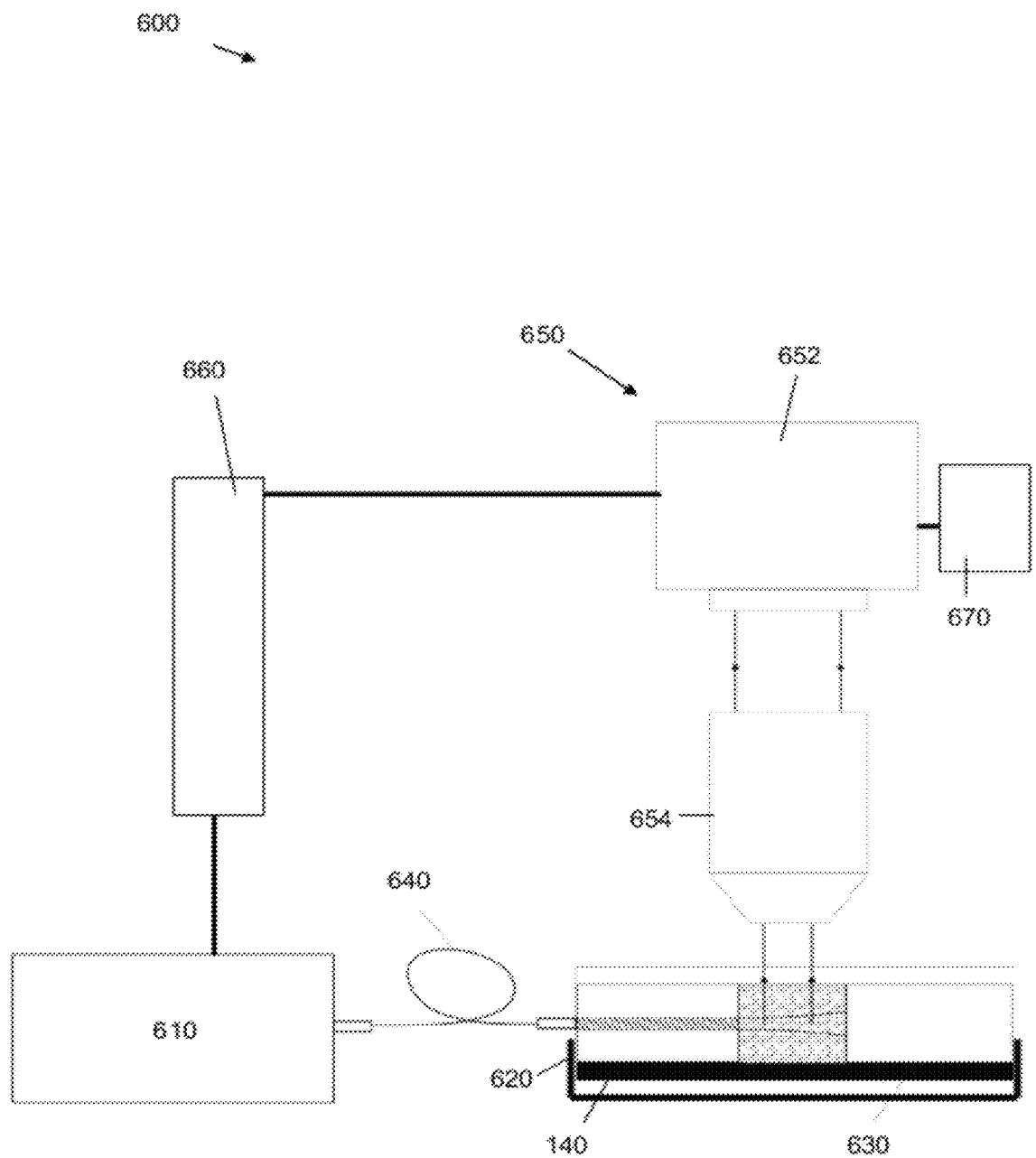
FIG. 7 illustrates a schematic representation of an imaging system according to an embodiment of the present invention.

By way of illustration, embodiments of the present invention not being limited thereto, further standard and/or optional features are discussed with reference to FIG. 7 illustrating an exemplary characterisation system 600.

The characterisation system 600 comprises a radiation source 610 for irradiating the sample. The radiation source may be any suitable radiation source for providing radiation to the sample. One type of examples of radiation sources that could be used are lasers, although the invention is not limited thereto. The wavelength or wavelength range used may be selected based on the application, e.g. based on the objects at which excitation or scattering is to be performed. The radiation source may be monochromatic or comprise a plurality of wavelengths. This may for example be a laser, a laserdiode, a VCSEL, an OLED, a nanolaser, a combination of laser sources, etc. In some examples, the radiation source also could be integrated in the device. It is an advantage that integrated radiation sources may relax the alignment conditions.

Figure 8:
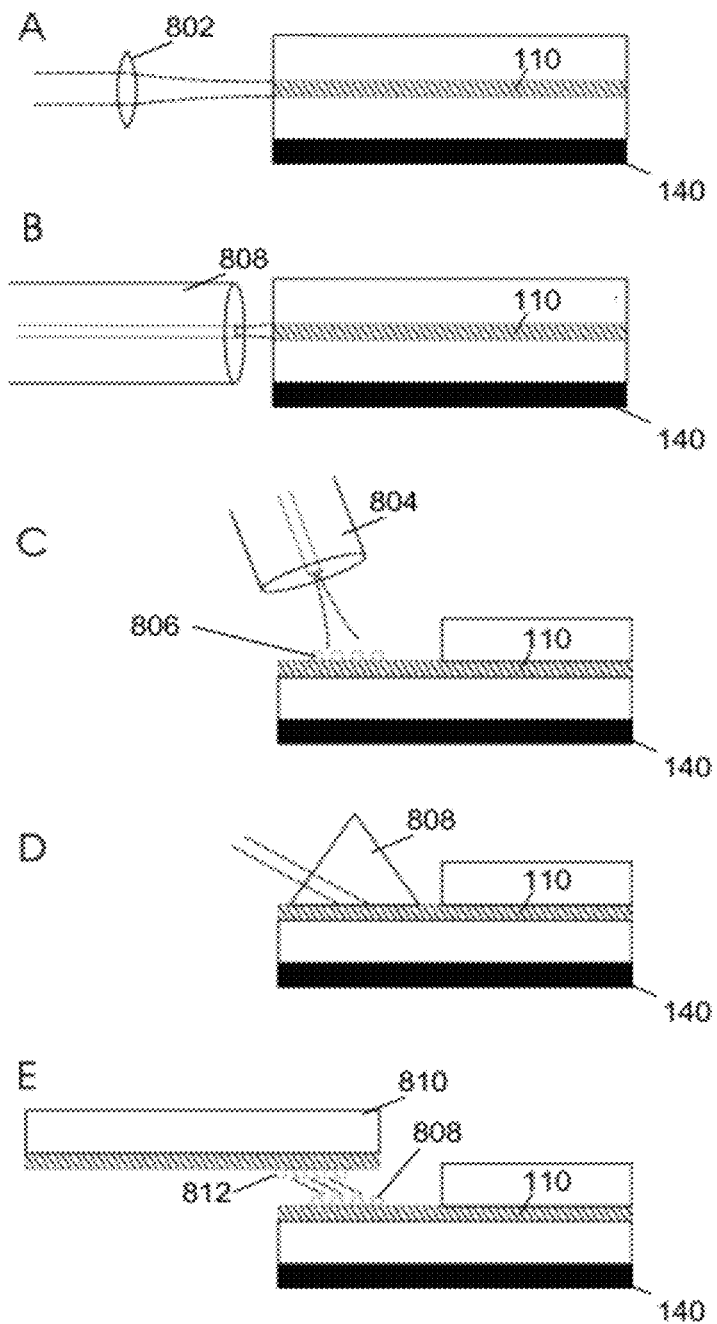
FIG. 8 illustrates different examples of possibilities to couple radiation into the integrated waveguide, such as using a cylindrical lens (A), using butt-coupling with an optical fibre (B), using a grating coupler (C), using a prism coupling (D), or using grating couplers (E), according to embodiments of the present invention.

The characterisation system 600 comprises a device holder 620, adapted for receiving an optical device 630 according to an embodiment as described above. Alternatively or in addition thereto, the imaging system 600 may comprise the optical device 630 itself. The effect of using an optical device is that sheet irradiation can be obtained in a reliable manner, resulting in an imaging, detection and/or characterisation technique allowing to obtain images with high contrast. Such a device holder 620 may comprise a positioning means for accurately positioning of the optical device 630, i.e. for alignment of the optical device 630 with respect to the radiation source 610. It is an advantage of embodiments according to the present invention that an improved alignment can be obtained, as part of the alignment is already fixed upfront in the optical device 630. Different waveguides can be stacked on top of each other to enable slices at different depths (z-coordinate) in the device. This can be done by sequentially coupling light to the different waveguides and simultaneously adjusting the height of the objective (z-direction) in order to keep an image in focus. This procedure has the advantage that the optical device does not contain moving parts. The imaging system 600 furthermore optionally may comprise a coupling means 640 for coupling the radiation to the planar waveguide in the optical device. Such coupling means for coupling the irradiation beam in an optical device. Alternatively, such coupling means may be part of the optical device. The coupling means 640 may for example be a coupling lens, such as for example a focusing lens like a cylindrical focusing lens or an optical fibre such as for example a butt-coupled optical fibre, an, optionally integrated, grating or a prism, etc. The radiation can be coupled into the waveguide from the edge of the substrate or from the top or bottom. Different embodiments can be realized and some are illustrated by way of example in FIG. 8. In example A the radiation from a laser is coupled by a cylindrical lens 802 onto the planar waveguide 110 on a substrate 140, by careful alignment. In example B the light of an optical fibre 804 is butt-coupled into the waveguide 110 on a substrate 140. In this case the width of the waveguide advantageously more or less matches the mode of the fibre to avoid losses. In example C the radiation of an optical fibre is irradiating a surface grating coupler 806, which couples the radiation into the planar waveguide 110 on a substrate 140. In this case, the alignment between the fibre and the substrate is less critical than in cases A or B. In example D the light of the radiation beam is entering a glass prism 808 and is coupled between the glass prism 808 and the planar waveguide 110 on a substrate 140 in a contact region between the glass prism and the planar waveguide 110. As in case C the lateral adjustment between laser beam and the substrate is not so critical. In example E the radiation of the radiation beam is coupled from a fixed planar waveguide 810 into air by a grating coupler 812 under a fixed angle and from air with a grating coupler 814 into the planar waveguide 110 on the substrate 140. In all these cases, the coupling is not perfect and some of the radiation is not coupled to the waveguide. A black layer or scattering layer on the bottom of the substrate can be used to reduce the influence of this light and to avoid that it might reduce the contrast of the measurement. The distance between the coupling region and the observation region may be between 0.1 and 100 mm. A longer waveguide will help to reduce the intensity of the light that is not coupled to the waveguide. In some embodiments, the planar waveguide may be thicker at the entrance side, i.e. the incoupling side, so that a more easy incoupling and less critical alignment may be obtained.

As indicated above, the present invention comprises or is adapted for operating with an optical device as described in embodiments according to the first aspect. Upon interaction between the illuminated object(s) and the incident radiation, a detection signal is generated. The latter may for example be a scattered illumination beam or a fluorescence response of the objects or labels attached thereto. The system may be adapted for capturing the detection signal in a direction perpendicular to the illumination sheet, i.e. in the direction of the reduced height of the irradiation sheet. The detection system 650 used typically may comprise a detecting element 652 such as for example a CCD chip, although the invention is not limited thereto, and may comprise optical components 654 such as an objective lens for capturing the detection signal. The detection system can for example be a lens-based microscope or another optical detection system whereby the focal plane typically may coincide with the irradiation sheet in order to obtain the high contrast images. The detection system also could be based on an on-chip lens-less method, such as a microfluidics microscope system.

The system 600 furthermore may comprise a controller 660 for controlling the irradiation and detection components and an optional positioning system. In embodiments where an electric field can be generated for inducing motion or trapping of objects in the medium, the controller 660 also may be adapted for controlling an electric field generator for inducing the electric field, whereby the electric field generator or the power source thereof also may be part of the system. Furthermore the system 600 also may comprise a processor 670 for processing the obtained images and an output port for outputting the images or a characteristic based thereon. Other components, such as for example filters, also can be provided, as will be known to the person skilled in the art.

It is an advantage of embodiments according to the present invention that a system is provided that allows creation of the sheet illumination to be performed in an integrated planar waveguide of the optical device, as the latter reduces the number of optical components required in the characterization system. Furthermore, the integrated planar waveguide allows to transport the light in a thin layer (only a few µm in height) over a distance of tens of millimeters with low losses. This has the advantage that it allows to couple in the light at a distance far from the actual detection region, thus making the set-up much more easy to accomplish and more flexible as compared to a macroscopic set-up where bulky lenses are needed at a close distance to the measurement chamber for generating the light sheet and for collecting the detection signal. In addition, the concept of generating a light sheet illumination by an integrated waveguide is amenable for integration into lab-on-a-chip devices, which is not the case for the classic set-up using macroscopic lens systems. Also, contrary to lens-based systems, the integrated waveguide concept is much more amenable for miniaturization, thus enabling applications such as high quality sheet illumination for miniature sensor probes.

Figure 9:
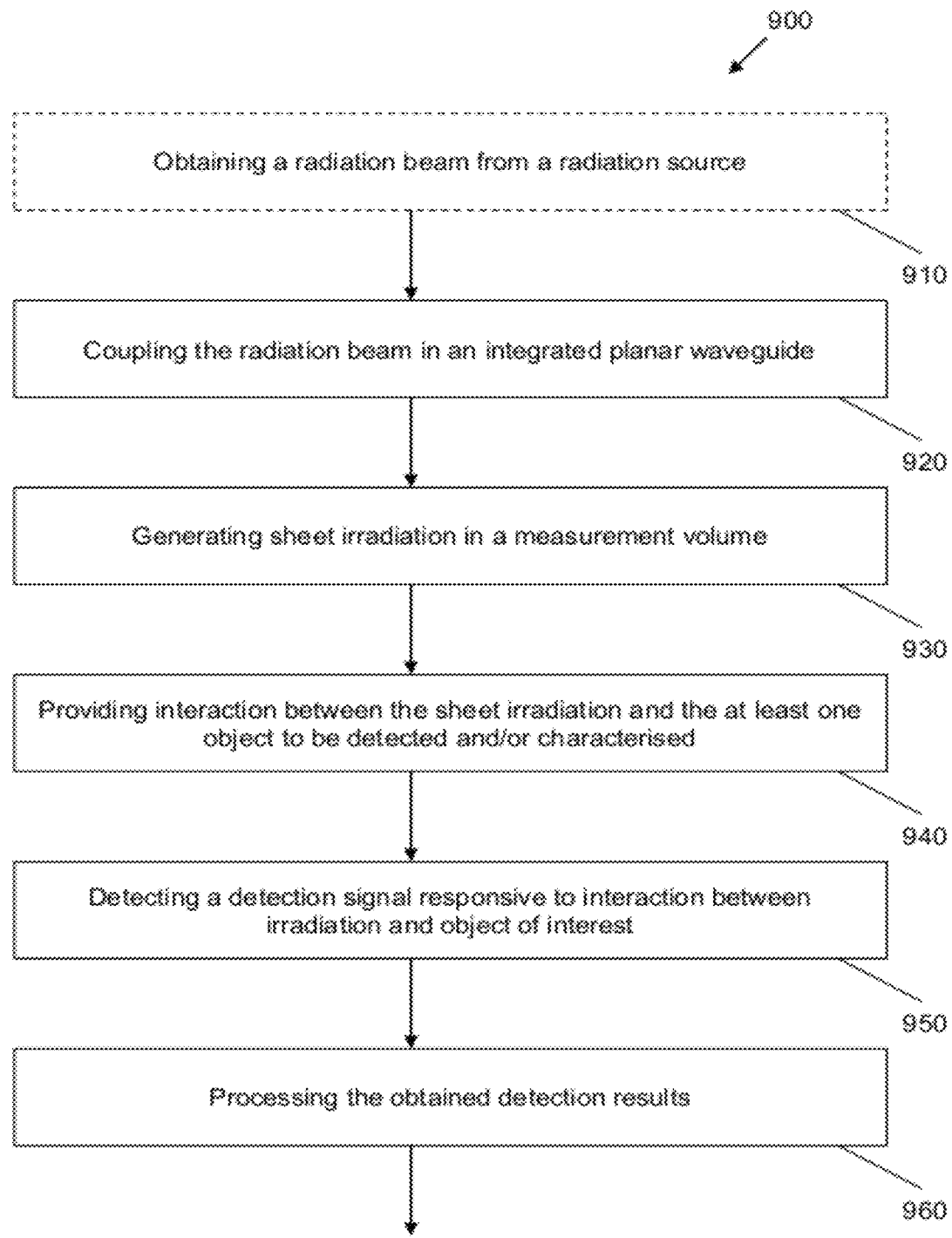
FIG. 9 illustrates a flow chart of a method for imaging objects, according to an embodiment of the present invention.

In a fourth aspect, the present invention also relates to a method for detecting or imaging or characterizing objects in a medium, e.g. a fluid. The method may be especially suitable for characterization, e.g. physicochemical properties, of particles suspended in a fluid or for obtaining information of parts of objects. The method may be especially suitable for being performed on a system as described in the second aspect or for being performed using a device as described in embodiments of the first aspect. Methods according to embodiments of the present invention may comprise optional and standard steps as described with reference to FIG. 9, illustrating an exemplary method 900 for detecting or imaging. The method may comprise obtaining 910 a radiation beam using a radiation source. According to embodiments of the present invention, the method may comprise coupling 920 the radiation beam to an integrated planar waveguide and generating sheet irradiation 930 in a measurement region, e.g. a fluidic channel, comprising a medium with at least one object to be characterized, thus providing interaction 940 between the sheet illumination and the object to be characterized. The method furthermore comprises detecting 950 a detection signal responsive to interaction of the sheet irradiation and the object to be characterized. In an optional step, the method comprises processing the obtained detection results 960 for deriving physicochemical properties. In optional steps, during the interaction step, the objects may be controlled, e.g. using an electrical field, another optical field, etc. The method furthermore may comprise steps expressing the functionality of components of the device according to the first aspect or the system according to the second aspect.

By way of illustration, embodiments of the present invention not being limited thereto, a number of particular examples and applications will be discussed in more detail.

Figure 10A:
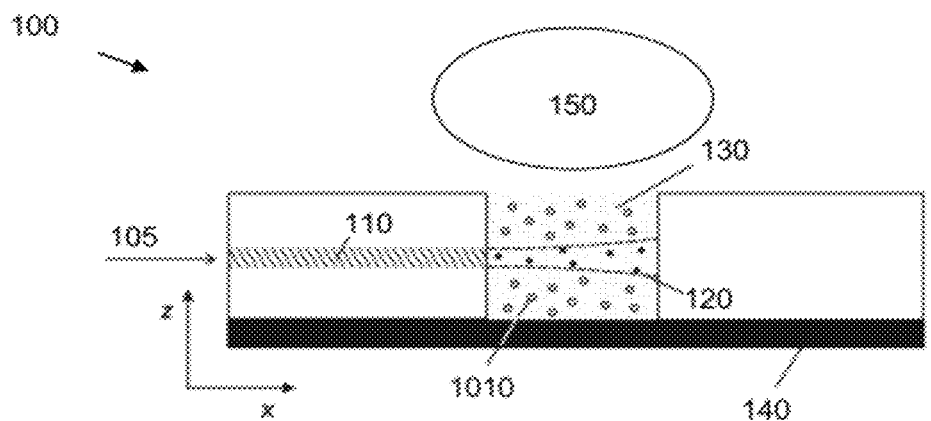
FIG. 10A and FIG. 10B illustrate a side view of an optofluidics device according to an embodiment of the present invention.
Figure 10B:
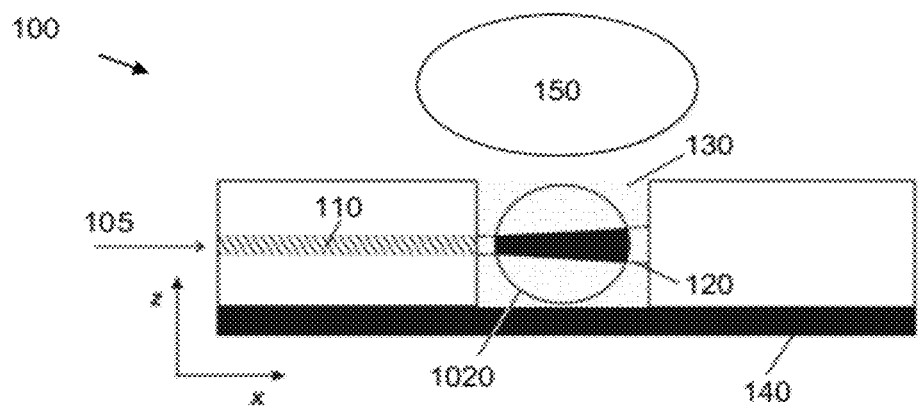

In a first particular example, a device and system and for physicochemical characterization of dispersed particles or larger objects is described. The system may be an imaging, detection and/or characterization system comprising components as described in any of the above embodiments. In the system according to the present example, sheet irradiation optical devices, such as for example sheet irradiation optofluidics devices, according to an embodiment of the present invention can be used for measuring physicochemical properties of dispersed particles or for assisting therein. Detection can for example be based on fluorescence or scattering of individual particles if their concentration is sufficiently low, although other techniques as described above also can be used. It is an advantage of applying sheet irradiation that contrast of the fluorescence of single particles can be substantially improved compared to normal epi-fluorescence illumination. The latter can be achieved because the sheet of light can selectively irradiate the focal plane of the observation objective lens, thus reducing out-of-focus fluorescence. The latter is illustrated in FIG. 10A and FIG. 10B comprising similar components as indicated above. From FIG. 10A it can be seen that using the sheet irradiation optical devices and using the imaging, detecting and/or characterization system according to the present example, irradiation of particles 1010 is restricted to those particles present in the irradiation sheet and only these particles generate a signal. From FIG. 10B it can be seen that using the sheet irradiation, only a part of the object 1020 is irradiated, resulting in the possibility of optical sectioning. Using the system and/or the devices, information can be obtained e.g. regarding the presence as well as motion parameters, such as for example translational and rotational motion parameters, fluorescence intensity (if fluorescence is used as imaging technique) and/or scattered light distribution. This may result in information regarding the size, the anisotropy and the concentration. Size may for example be derived from studying the Brownian motion which may be detected and/or imaged using the system and/or or device as described.

Figure 11A:
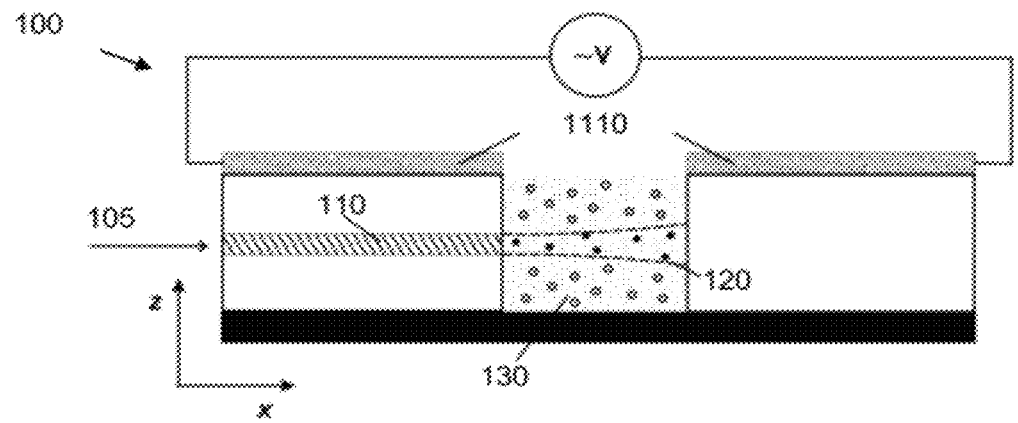
FIG. 11A and FIG. 11B illustrates a side view and a schematic top view of an optofluidics device comprising electrodes, according to an embodiment of the present invention.
Figure 11B:
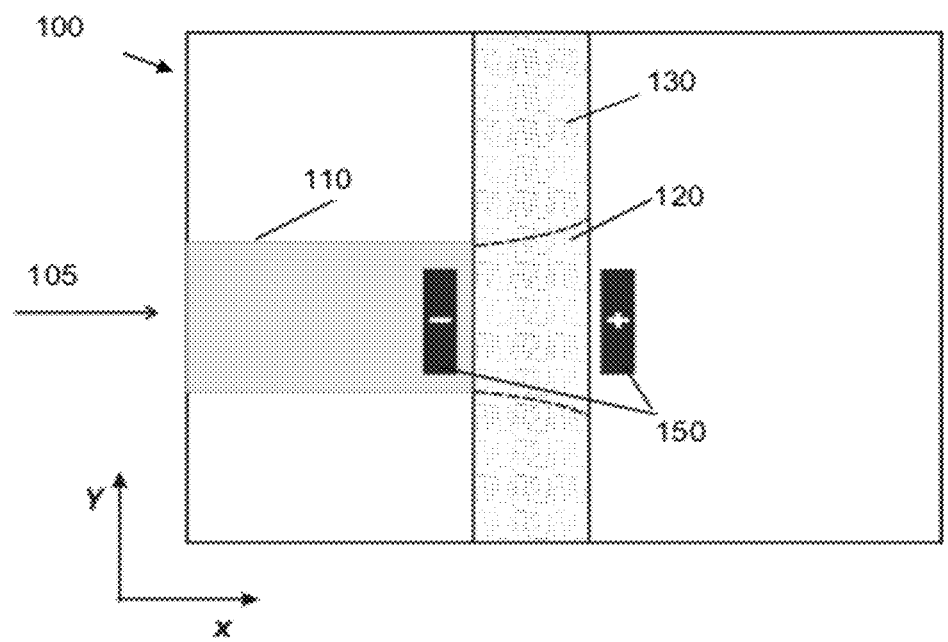

In a second particular example, a device and system are described for physicochemical characterization of dispersed particles. The device and/or system may be adapted for applying an electric field, e.g. a varying electric field or alternating electric field, for analyzing motion of particles as described above in such electric fields. Such devices and/or systems are especially suitable for deriving the zeta-potential of particles. The electric field can be generated by electrodes applied on the sheet illumination optical chip. As can be seen in the example of FIGS. 11A and 11B, electrodes 1110 may be applied at both sides of the measurement region 130 and will be preferably applied in the x-direction, i.e. perpendicular to the flow direction, so that the particle trajectory remains in the plane of focus during the motion. By determining the properties on a particle-by-particle basis, a more accurate distribution can be obtained compared to existing ensemble techniques, such as photon counting correlation spectroscopy. Particles typically can have a size in the range of 1 nm to 10 µm, where the upper limit is determined by the difference in density between the particle and the fluid, to avoid sedimentation. If the particles are labelled with e.g. a fluorophore, their size and zeta potential can be measured in biological fluids, such as blood, which is not possible with light scattering techniques. In a third particular embodiment, the method for detecting and/or characterizing and/or imaging is applied for monitoring the interaction of particles. The method may be used for detecting or imaging or characterizing two or more sub-populations of particles labelled with spectrally different fluorophores. The detecting or imaging and/or characterizing allows monitoring the interaction of two or more sub-populations. The detecting or imaging or characterizing also may assist in dynamic co-localisation analysis. If the concentration is too high for individual particles to be resolved by the detection system, information on the concentration and motion parameters can be obtained by ensemble analysis techniques, such as image correlation spectroscopy.

Figure 5B:
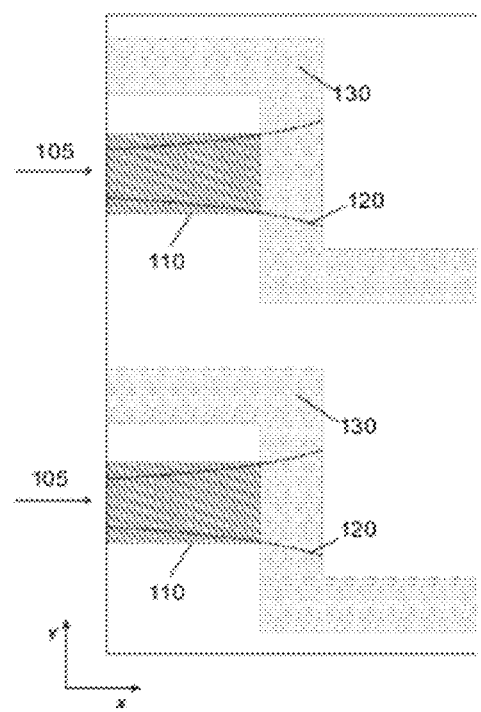

In a fourth particular embodiment, the present invention relates to a method for characterizing and/or imaging at least one object, whereby the method is adapted for performing image flow cytometry. The aim of image flow cytometry is to image and count objects such as for example cells in a fluid stream, either in bright field or fluorescence mode, and to extract physical and/or chemical information from that on a single cell basis. The advantage of sheet irradiation in this context is that optical sections can be recorded from the cells with better contrast and a lower detection limit as compared to the normal wide-field images. The principle also is illustrated by FIG. 5B, illustrating imaging of sections of an object. Imaging also could be done in dark field (based on scattered light) or fluorescence mode, resulting in confocal-like images of the cells. The technique therefore allows to record selectively light coming from a section of the object, resulting in images having a reduced background signal, which results in an improved contrast and a lower detection limit.

Figure 12:
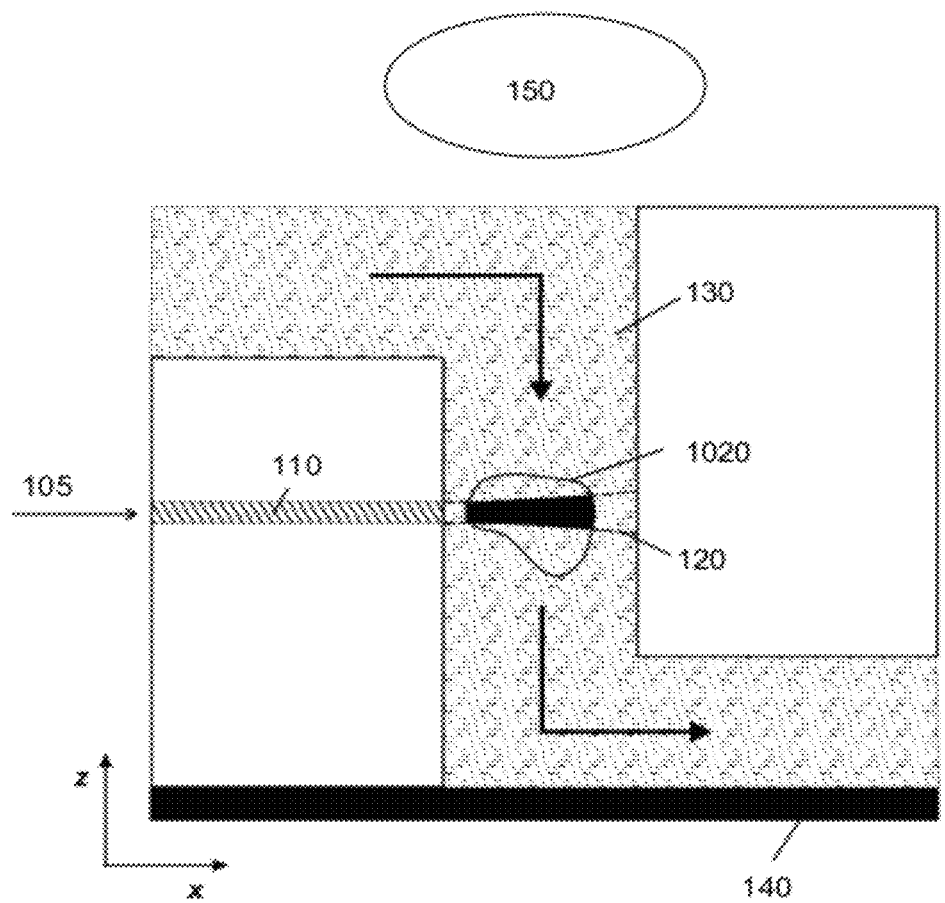
FIG. 12 illustrates an example of a method for obtaining sectional information of an object, according to an embodiment of the present invention.

In a fifth particular embodiment, the present invention relates to a method for characterizing and/or imaging at least one object, whereby the method is used for obtaining 3 dimensional information of an object 1020. The latter can be obtained by obtaining information of a plurality of sections through the object, e.g. by transporting the object through the sheet irradiation 120, preferably in a direction perpendicular to the irradiation plane 120. The principle thereof is shown in FIG. 12. In a sixth particular embodiment, the present invention relates to a method for characterizing and/or imaging at least one object, used for particle image velocimetry. This is an optical method of fluid visualization. It is used to obtain instantaneous velocity measurements and related properties in fluids. The fluid is seeded with tracer particles whose motion is used to calculate velocity information of the flow being studied. In case the particle concentration is sufficiently low such that individual particles can be tracked, the method may be referred to as particle tracking velocimetry (PIV). PIV can be performed using an irradiation sheet 120 configuration similar to the one described in FIG. 10A and FIG. 10B. The use of an integrated planar waveguide could, therefore, be used as a convenient means to track the position of particles and e.g. to study flow profiles in microfluidics devices.

By way of illustration, embodiments of the present invention not being limited thereby, a number of experimental results are provided.

Figure 13A:
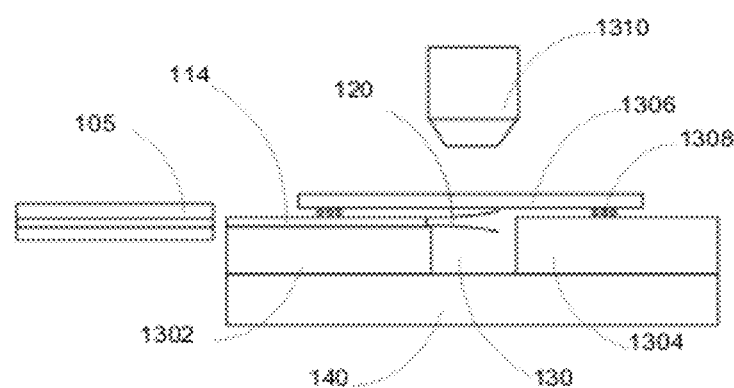
FIG. 13A and FIG. 13B illustrate a side view respectively top view of an optofluidics device being an example of an embodiment according to the present invention.
Figure 13B:
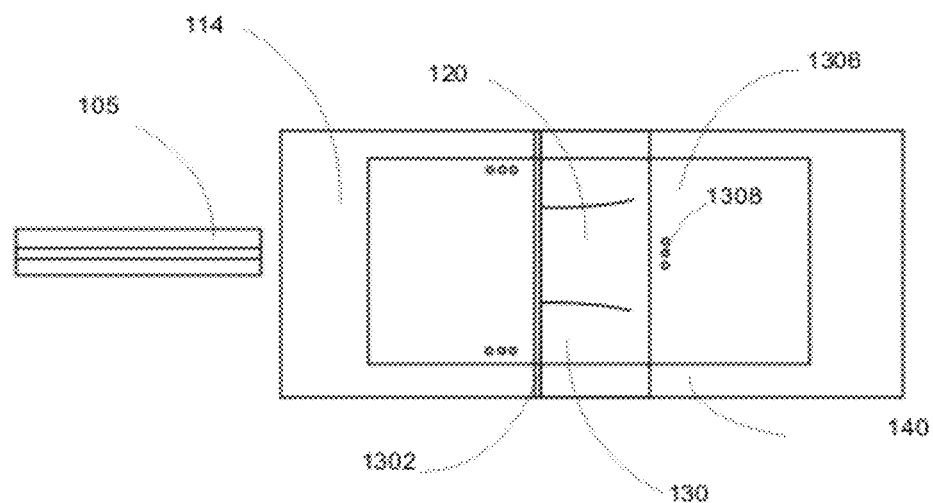

In a first example, manufacturing of a particular microfluidics device is shown. The microfluidics device according to the present example is a hybrid device. The device is illustrated in FIG. 13A and FIG. 13B in side view as well as in top view. An advantage of the method illustrated by the present example and of examples thus obtained is that sharp edges can be obtained for the planar waveguide, allowing better irradiation characteristics of the device. The planar waveguide was formed by a glass substrate 1302 with a polymer coating on top. The bottom cladding layer 1302 of the planar waveguide was the glass substrate (refractive index 1.52), a polymer SU-8 2010 (refractive index 1.60) was used as core 114 material and either air (refractive index 1.00) or water (refractive index 1.33) was used as the top cladding. The glass substrate 1302 of the present example had sides with a length of 2.54 cm and a thickness of 0.11 cm. The glass substrate 1302 was first rinsed with acetone, isopropanol and deionized water (in that order). The surface was dehydrated by baking on a hotplate at 120° C. for 10 minutes. TI Prime was spin coated on the glass substrate 1302 at 4000 rpm for 30 s to promote the adhesion of the SU-8. The substrate 1302 with adhesion promoter was baked on a hotplate at 120° C. for 10 minutes. Next, the SU-8 2010 coating was applied by spinning 1 ml of the polymer at 5500 rpm for 40 s, resulting in a layer thickness around 8 µm. The SU-8 coated substrate was baked on a hotplate at 60° C. for 6 minutes and then at 90° C. for 9 minutes. After cooling down, the SU-8 was cured by exposing to UV light for 10 s. A mask was used to prevent exposure of a micrometer wide strip at one side of the waveguide. A post exposure bake on a hotplate at 60° C. for 6 minutes and then at 90° C. for 9 minutes was done for cross-linking the exposed part of the SU-8. The strip of SU-8 that was not exposed to UV was etched by immersion in SU-8 Developer for 15 s. The developed surface was rinsed afterwards with isopropanol and deionized water. The side of the planar waveguide where a sharp edge of SU-8 was obtained, is the side of the waveguide where the sheet of light 120 is produced. A channel 130 was constructed next to this side of the waveguide by gluing the glass substrate 1302 on top of a larger substrate 140 next to an glass substrate 1304 identical to the waveguide (without SU-8 coating), forming a 1 mm wide channel 130 in between both glass substrates 1302, 1304. The channel 130 was sealed by gluing a microscopy cover slip 1306 onto both glass substrates. A 10 µm distance between the cover slip and the waveguide surface was maintained by spacers 1308. FIG. 13A and FIG. 13B also illustrate a collecting lens 1310 for collecting radiation from the irradiated sample. Irradiation of the sample was performed via a radiation source 105, in the present case being a fibre at one side coupled to a laser.

Figure 14:
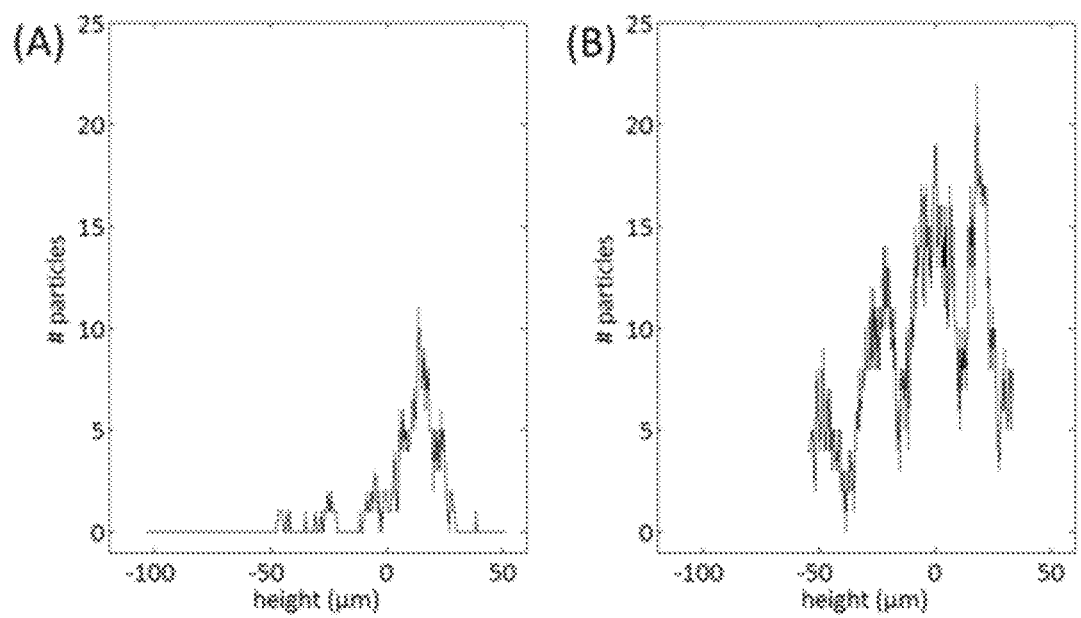
FIG. 14 illustrates measurement results for sheet illumination (A) and widefield epi illumination (B) for detection of fluorescent particles, as can be obtained using a device according to an embodiment of the present invention.

In further experimental results, the irradiation properties of irradiation obtained using a system as shown in FIG. 13A are discussed and compared to widefield epi irradiation. For obtaining experimental results for sheet irradiation, laser light (639 nm) was coupled into an FC connector of the single mode fiber with a fiber coupler. The other side of the fiber was not connectorized and was used to couple the laser light into the side of the planar waveguide opposite to the channel. Alignment of the fiber core with the waveguide core was achieved by a precision fiber alignment stage. The micro-illuminator and alignment stage together were placed next to a widefield epi-fluorescence microscope. To image the channel, a 40× plan apo NA 0.95 objective lens was placed above the cover slip of the micro-illuminator using an objective invertor, as illustrated in FIG. 13A. Fluorescence light coming from the sheet of light in the channel was collected by the objective lens and sent towards a CCD camera. One pixel on the 512 by 512 pixel CCD chip corresponds to a distance around 0.2 µm in the channel. The sheet of light was observed indirectly by looking at 0.2 µm diameter dark red fluorescent microspheres freely diffusing in the micro-illuminator channel. Using the motorized z-stage of the microscope, z-stacks over a height difference of 100 µm were recorded with a step of 0.5 µm. The field of view was around 100 µm by 100 µm. Two concentrations of the microspheres were used, estimated around $2.25 \cdot 10^{10}$ #/ml and $9.10 \cdot 10^{10}$ #/ml. FIG. 14 shows the amount of detected particles in a sub-region of the image as function of the z-position in the case of both sheet irradiation and widefield irradiation. In the case of sheet illumination, there was a z-distance of around 30 µm where at least two particles were visible. The thickness of the sheet, defined as the full width at half maximum of the peak in FIG. 14, is around 20 µm. For widefield illumination several particles were visible at each z-position, but the number of particles decreases going further from the cover slip. This effect was caused by increasing scattering and absorption of the emitted fluorescence and also by increasing spherical aberration resulting in lower contrast.

There are different ways to quantify the difference between the two illumination types. The contrast can be defined as (definition A)

$$A = \frac{I_p - I_b}{I_p + I_b}$$

with $I_p$ the average particle intensity above the offset value and $I_b$ the average background intensity above the offset value. Another straightforward contrast definition used can be the intensity background ratio, defined as (definition B)

$$B = \frac{I_p}{I_b}$$

TABLE 1

| concentration (#/ml) | contrast | Sheet | Widefield | improvement |
|---|---|---|---|---|
| $2.25 \cdot 10^{10}$ | definition A | 0.30 ± 0.03 | 0.146 ± 0.006 | 2.0 ± 0.2 |
| | definition B | 2.0 ± 0.1 | 1.36 ± 0.01 | 1.47 ± 0.07 |
| $9.10 \cdot 10^{10}$ | definition A | 0.22 ± 0.02 | 0.078 ± 0.007 | 2.8 ± 0.4 |
| | definition B | 1.59 ± 0.08 | 1.17 ± 0.09 | 1.4 ± 0.1 |

The results given in Table 1, indicate the contrast and intensity to background ratio for both concentrations of microspheres, both for sheet and for widefield epi illumination. For the higher concentration, the contrast for sheet illumination improves 2.8 times compared to widefield illumination. The signal background ratio is around 1.5 times better in the sheet illumination case. The improvement in signal noise ratio is roughly the same for the lower concentration, but the gain in contrast is not as high. For smaller concentrations a smaller difference between both illumination types can be expected.

Figure 15A:
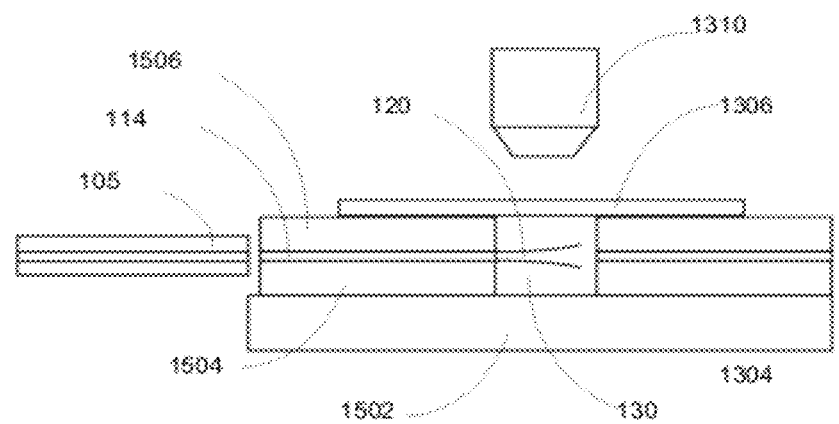
FIG. 15A and FIG. 15B illustrate a side view respectively top view of an optofluidics device being another example of an embodiment according to the present invention.
Figure 15B:
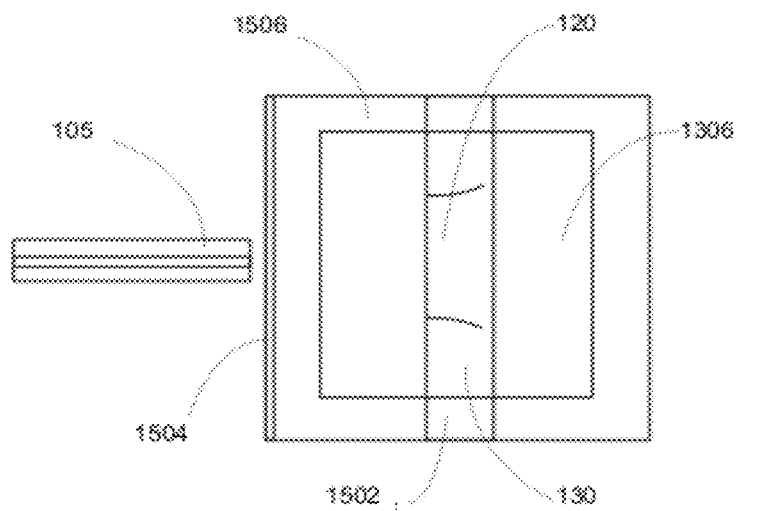

In a third example, manufacturing of another particular microfluidics device is shown. The microfluidics device according to the present example is a monolithic integrated device. The device is illustrated in FIG. 15A and FIG. 15B in side view as well in top view. The planar waveguide is a 3 layer polymer coating on top of a glass substrate 1502. The polymer SU-8 2010 is used for the middle core 114 layer, the bottom cladding layer 1504 and top cladding layer 1506 are formed by SU-8 2010 diluted with 6% aliphatic resin, resulting in a refractive index that is 0.005 lower than pure SU-8 2010. The glass substrate 1502 in the present example has 2.54 cm sides and a thickness of 0.11 cm.

The glass substrate 1502 was first rinsed with acetone, isopropanol and deionized water (in that order). The surface was dehydrated by baking on a hotplate at 120° C. for 10 minutes. TI Prime was spin coated on the glass substrate at 4000 rpm for 30 s to promote the adhesion of the SU-8. The substrate with adhesion promoter was baked on a hotplate at 120° C. for 10 minutes.

Next, the first cladding layer 1504 was applied by spinning 1 ml of the SU-8 2010 diluted with resin at 2500 rpm for 40 s, resulting in a layer thickness around 12 µm. The coated substrate was baked on a hotplate at 60° C. for 6 minutes and then at 90° C. for 9 minutes. After cooling down, the core layer 114 was produced by spinning 1 ml of SU-8 2010 without resin on top of the first cladding layer 1504 at 5500 rpm for 40 s, resulting in a layer thickness around 8 µm. Again the coated substrate was baked on a hotplate at 60° C. for 6 minutes and then at 90° C. for 9 minutes. Subsequently, the procedure to form the first cladding layer 1504 was repeated to form the second cladding layer 1506.

After cooling down, the 3 layer SU-8 structure was cured by exposing to UV light for 15 s. A mask was used to prevent exposure of a micrometer wide strip at one side of the waveguide and a 100 µm wide strip approximately in the middle of the waveguide. A post exposure bake on a hotplate at 60° C. for 6 minutes and then at 90° C. for 9 minutes was required to cross-link the exposed part of the SU-8. The parts of the SU-8 that were not exposed to UV were etched by immersion in SU-8 Developer for 30 s. The developed surface was rinsed afterwards with isopropanol and deionized water. In this way, the 100 µm wide strip in the planar waveguide that is etched by photolithography as described above can be used as the channel 130 in which the sheet of light 120 can produced. The channel 130 is sealed by placing a microscopy cover slip 1306 onto the waveguide. The side of the planar waveguide where a sharp edge of SU-8 has been obtained by photolithography (as described in section 1) is the side where the light is coupled into the waveguide.

In further experimental results, the irradiation properties of irradiation obtained using a system as shown in FIG. 15A are discussed and compared to widefield epi irradiation. For obtaining experimental results for sheet irradiation, laser light (639 nm) was coupled into the FC connector of a single mode fiber with a fiber coupler. The other side of the fiber was not connectorized and is used to couple the laser light into the side of the planar waveguide opposite to the channel. Alignment of the fiber core with the waveguide core was achieved by a precision fiber alignment stage. The micro-illuminator and alignment stage together were placed next to a widefield epi-fluorescence microscope. To image the channel, a 40× plan apo NA 0.95 objective lens was placed above the cover slip of the micro-illuminator using an objective invertor. Fluorescence light coming from the sheet of light in the channel was collected by the objective lens and sent towards a CCD camera. One pixel on the 512 by 512 pixel CCD chip corresponds to a distance around 0.2 µm in the channel.

Figure 16:
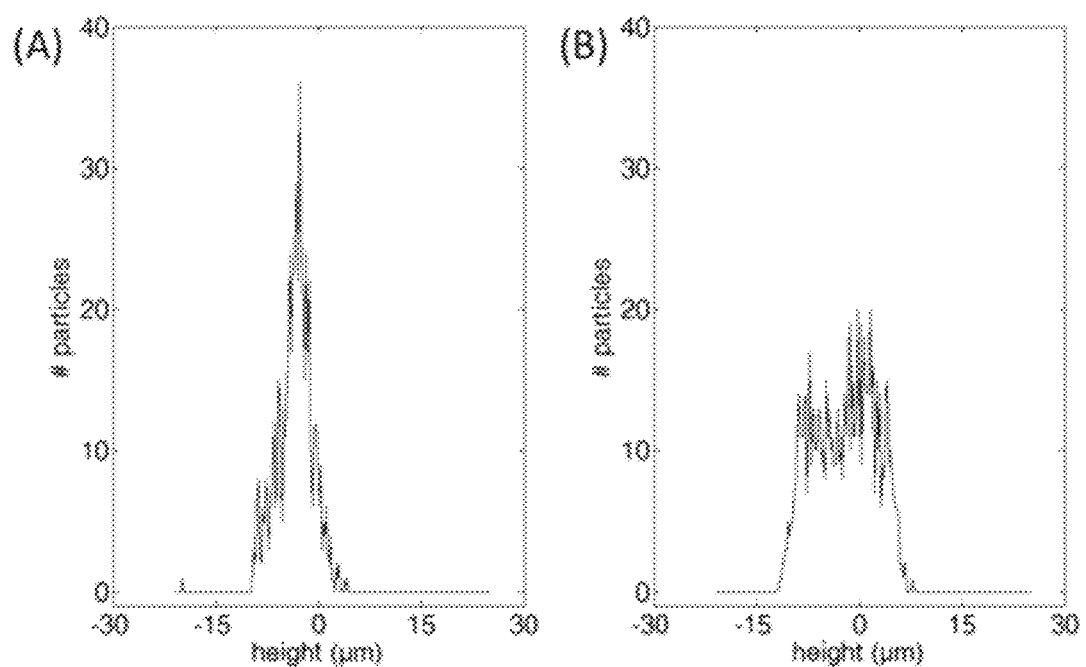
FIG. 16 illustrates measurement results for sheet illumination (A) and widefield epi illumination (B) for detection of fluorescent particles, as can be obtained using a device according to an embodiment of the present invention.

The sheet of light was observed indirectly by looking at 0.2 µm diameter dark red fluorescent microspheres freely diffusing in the micro-illuminator channel. Using the motorized z-stage of the microscope, z-stacks over a height difference of 46 µm with a step of 0.2 µm were recorded by the microscope stage controller. The field of view was around 100 µm by 100 µm. The concentration of the microspheres is estimated around $4.55 \cdot 10^{10}$ #/ml. FIG. 16 shows the amount of detected particles in a subregion of the image in function of the z-position in the case of both sheet irradiation and widefield irradiation. In the case of sheet illumination, there is a z-distance of around 13 µm where at least two particles are visible. The thickness of the sheet, defined as the full width at half maximum of the peak in FIG. 16, is around 6 µm. For widefield illumination several particles are visible over a wider z-range of 19 µm and there is no pronounced peak.

TABLE 2

| contrast | Sheet | Widefield | improvement |
|---|---|---|---|
| definition A | 0.54 ± 0.05 | 0.39 ± 0.04 | 1.4 ± 0.2 |
| definition B | 3.8 ± 0.6 | 2.4 ± 0.2 | 1.6 ± 0.3 |

Using the same definitions as for the above examples, it was found that the contrast for sheet illumination improves 1.4 times compared to widefield illumination. The signal background ratio is around 1.6 times better in the sheet illumination case. The results given in Table 2, indicate the contrast intensity to background ratio values for fluorescent 0.2 µm diameter microspheres. The values were determined based on three images of a z-stack chosen in the middle of the sheet of light and 3 images at the same height for the widefield irradiation were used. In each image typically 20 to 40 particles were analyzed.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The foregoing description details certain embodiments of the invention. It will be appreciated, however, that no matter how detailed the foregoing appears in text, the invention may be practiced in many ways, and is therefore not limited to the embodiments disclosed. It should be noted that the use of particular terminology when describing certain features or aspects of the invention should not be taken to imply that the terminology is being re-defined herein to be restricted to include any specific characteristics of the features or aspects of the invention with which that terminology is associated.

The invention claimed is:

1. An optical device for irradiating at least one object in a medium,
    the optical device comprising at least one integrated planar waveguide arranged to provide sheet irradiation in a measurement region;
    wherein the at least one integrated waveguide defining an irradiation sheet has a height in a first direction perpendicular to the propagation direction of radiation in the at least one integrated waveguide, the height being at least three times smaller than a width in a second direction perpendicular to the propagation direction of radiation in the at least one waveguide; and
    wherein the optical device is configured for allowing detection of a response to the sheet irradiation in a direction perpendicular to the irradiation sheet.

2. The optical device according to claim 1, the integrated waveguide being arranged to support a single laser mode.

3. The optical device according to claim 1, wherein the device is configured to detect a response signal from the at least one object being irradiated in the measurement region.

4. The optical device according to claim 1, said medium comprising a fluidic sample, the device furthermore comprising at least one transportation channel for transportation of the medium comprising the at least one object of interest, the transportation channel containing or being in contact with the planar waveguide such that a sheet of irradiation is generated within the channel or a part thereof forming the measurement region.

5. The optical device according to claim 4, the transportation channel being an integrated microfluidics channel, wherein the optical device is an optofluidics device and the measurement region is part of the integrated microfluidics channel of the optofluidics device.

6. The optical device according to claim 4, wherein the at least one integrated planar waveguide has a core defined by two major surfaces, wherein none of the major surfaces lies in plane with a bottom surface of the transportation channel.

7. The optical device according to claim 4, wherein the optical device comprises a substrate layer, an integrated planar waveguide and a second component being attached to the substrate layer, and wherein the integrated planar waveguide and second component are arranged so that the transportation channel is substantially formed from the substrate layer, the integrated planar waveguide and the second component.

8. The optical device according to claim 1, the optical device furthermore comprising electrodes providing an electric field in a direction perpendicular to a transportation direction of the at least one object of interest.

9. The optical device according to claim 1, the optical device comprising a plurality of measurement regions, wherein the device is arranged to image a plurality of objects in different measurement regions.

10. The optical device according to claim 1, wherein the optical device comprises two integrated waveguides at opposite sides of the measurement region, said waveguides being configured so that their sheet illumination coincides.

11. The optical device according to claim 1, wherein the optical device comprises two integrated waveguides at opposite sides of the measurement region, said waveguides being configured so that their sheet illumination does not coincide.

12. A characterisation system for characterising at least one object in a medium, the characterisation system cooperating with or comprising an optical device according to claim 1, the characterisation system comprising a radiation source generating a radiation beam irradiating the at least one object using said optical device and a detection system detecting a response due to interaction of the at least one object with the irradiation sheet generated using the optical device, wherein the detection system is configured to detect the signal in a direction perpendicular to an average plane through the irradiation sheet.

13. The characterisation system according to claim 12, wherein the detection system is configured so that the focal plane of the detection system for capturing the detection signal coincides with the irradiation sheet.

14. The characterization system according to claim 12, the system furthermore comprising coupling devices arranged to couple radiation into the waveguide of the optical device.

15. The characterization system according to claim 12, wherein the radiation source is integrated in the optical device.

16. A method for characterising an object in a medium, the method comprising
    generating sheet irradiation in a measurement region using an integrated planar waveguide, wherein the at least one integrated waveguide defines an irradiation sheet having a height in a first direction perpendicular to the propagation direction or radiation in the at least one integrated waveguide, the height being at least three times smaller than a width in a second direction perpendicular to the propagation direction of radiation in the at least one waveguide,
    providing interaction between the sheet irradiation and at least one object to be characterised, and
    detecting a signal responsive to interaction between the sheet irradiation and the object of interest in a direction perpendicular to the irradiation sheet.

17. The method according to claim 16, wherein the method furthermore comprises coupling a radiation beam in the integrated planar waveguide.

* * * * *